(12) United States Patent
Zhadkevich

(10) Patent No.: US 10,219,807 B2
(45) Date of Patent: Mar. 5, 2019

(54) OCCLUDING CATHETER FOR PREVENTION OF STROKE

(71) Applicant: Michael Zhadkevich, Inman, SC (US)

(72) Inventor: Michael Zhadkevich, Inman, SC (US)

( * ) Notice: Subject to any disclaimer, the term of this patent is extended or adjusted under 35 U.S.C. 154(b) by 63 days.

(21) Appl. No.: 15/298,285

(22) Filed: Oct. 20, 2016

(65) Prior Publication Data

US 2017/0035431 A1 Feb. 9, 2017

Related U.S. Application Data

(62) Division of application No. 13/918,492, filed on Jun. 14, 2013, now Pat. No. 9,498,225.

(Continued)

(51) Int. Cl.
*A61M 29/00* (2006.01)
*A61B 17/12* (2006.01)
(Continued)

(52) U.S. Cl.
CPC .... *A61B 17/12109* (2013.01); *A61B 17/1204* (2013.01); *A61B 17/12031* (2013.01);
(Continued)

(58) Field of Classification Search
CPC ........ A61B 17/12031; A61B 17/12036; A61B 17/12109; A61B 17/12136;
(Continued)

(56) References Cited

U.S. PATENT DOCUMENTS 2,676,586 A 4/1954 Coakwell, Jr.
3,585,983 A 6/1971 Kantrowitz
(Continued)

FOREIGN PATENT DOCUMENTS

EP 0 203 310 A2 3/1986
EP 1 891 902 A1 2/2008
(Continued)

OTHER PUBLICATIONS

European Patent Office; Extended European Search Report; European Application No. 14166170.2-1654; European Patent Office; pp. 1-7; publisher European Patent Office; Published Munich Germany; copyright and dated Jul. 28, 2014; copy in parent application (7 pages).

Wikipedia; "Pulmonary artery catheter Pulmonary artery catheter", Wikipedia, The Free Encyclopedia., May 12, 2012, XP055235920, Retrieved from the Internet:URLhttps://en.wikipedia.org/w/index. php?title=Pulmonary_artery_catheter&oldid+694424669 [retrieved on Feb. 18, 2017] copy enclosed (5 pages).

(Continued)

*Primary Examiner* — Tuan V Nguyen
(74) *Attorney, Agent, or Firm* — J. Bennett Mullinax, LLC

(57) ABSTRACT

An occluding catheter for preventing stroke by occluding blood flow through right and left carotid arteries is provided. The occluding catheter includes a shaft that has a proximal end and a distal end, and a proximal occluding balloon carried by the shaft. The proximal occluding balloon is inflated to occlude blood flow through one of the right carotid artery and the left carotid artery. A distal occluding balloon is carried by the shaft and is inflated to occlude blood flow through one of the right carotid artery and the left carotid artery that is not occluded by the proximal occluding balloon. The shaft has a segment that is located between the proximal occluding balloon and the distal occluding balloon. Also provided is an alternative arrangement with a single occluding balloon, and an associated method of diverting emboli from cerebral circulation.

17 Claims, 12 Drawing Sheets

Related U.S. Application Data

(60) Provisional application No. 61/668,980, filed on Jul. 6, 2012.

(51) Int. Cl.
*A61M 25/10* (2013.01)
*A61M 25/09* (2006.01)
*A61B 17/22* (2006.01)
*A61M 25/00* (2006.01)

(52) U.S. Cl.
CPC .. *A61B 17/12036* (2013.01); *A61B 17/12045* (2013.01); *A61B 17/12136* (2013.01); *A61M 25/09* (2013.01); *A61M 25/10* (2013.01); *A61M 25/1002* (2013.01); *A61M 25/1011* (2013.01); *A61M 25/10184* (2013.11); *A61B 2017/12127* (2013.01); *A61B 2017/22067* (2013.01); *A61M 25/1018* (2013.01); *A61M 2025/0003* (2013.01); *A61M 2025/1052* (2013.01)

(58) Field of Classification Search
CPC ......... A61B 17/1204; A61B 17/12045; A61M 25/09; A61M 25/10; A61M 25/1002; A61M 25/1011
See application file for complete search history.

(56) References Cited

U.S. PATENT DOCUMENTS

| | | |
|---|---|---|
| 3,587,584 A | 6/1971 | Bourbon |
| 4,395,806 A | 8/1983 | Wonder |
| 4,676,232 A | 6/1987 | Olsson et al. |
| 4,745,924 A | 5/1988 | Ruff |
| 4,984,563 A | 1/1991 | Renaud |
| 5,059,177 A | 10/1991 | Towne |
| 5,271,409 A | 12/1993 | Millay |
| 5,360,403 A | 11/1994 | Mische |
| 5,441,051 A | 8/1995 | Hileman |
| 5,514,079 A | 5/1996 | Dilon |
| 5,741,295 A | 4/1998 | McEwen |
| 5,908,407 A * | 6/1999 | Frazee ............... A61M 25/1011 604/101.01 |
| 6,156,005 A | 12/2000 | Theron |
| 6,168,579 B1 | 1/2001 | Tsugita |
| 6,325,067 B1 | 12/2001 | Sterman et al. |
| 6,425,916 B1 | 7/2002 | Garrison et al. |
| 6,595,980 B1 | 7/2003 | Barbut |
| 7,250,025 B2 | 7/2007 | Nigroni |
| 7,374,531 B1 | 5/2008 | Kantrowitz |
| 7,458,980 B2 | 12/2008 | Barbut |
| 7,727,254 B2 | 6/2010 | Pab |
| 7,972,356 B2 | 7/2011 | Boyle et al. |
| D643,536 S | 8/2011 | Viverizo |
| 7,998,104 B2 | 8/2011 | Chang |
| 8,025,674 B2 | 9/2011 | Barbut et al. |
| 8,034,043 B1 | 10/2011 | Barbut |
| 8,061,562 B2 | 11/2011 | Carpenter |
| 9,795,470 B2 | 10/2017 | Ganesan |
| 2002/0115982 A1 | 8/2002 | Barbut |
| 2002/0173815 A1 | 11/2002 | Hogendijk |
| 2003/0036728 A1 | 2/2003 | Samson |
| 2003/0176884 A1 | 9/2003 | Berrada |
| 2005/0015048 A1 | 1/2005 | Chiu |
| 2005/0059931 A1 | 3/2005 | Garrison |
| 2005/0075531 A1 | 4/2005 | Loeb et al. |
| 2005/0154344 A1 | 7/2005 | Chang |
| 2005/0197624 A1 | 9/2005 | Goodson |
| 2009/0326575 A1 | 12/2009 | Galdonik |
| 2010/0113939 A1* | 5/2010 | Mashimo ........... A61B 5/02158 600/470 |
| 2010/0179583 A1 | 7/2010 | Carpenter et al. |
| 2010/0324589 A1 | 12/2010 | Carpenter et al. |
| 2011/0028934 A1 | 2/2011 | Buckman et al. |
| 2011/0054322 A1 | 3/2011 | Zanatta |
| 2011/0295114 A1* | 12/2011 | Agah ................ A61M 25/007 600/435 |
| 2011/0313445 A1 | 12/2011 | Galdonik |
| 2012/0179195 A1 | 7/2012 | Lashinski |
| 2012/0203265 A1 | 8/2012 | Heuser |
| 2013/0023909 A1 | 1/2013 | Duhay |
| 2013/0184742 A1 | 7/2013 | Ganesan et al. |
| 2014/0024955 A1 | 1/2014 | Zhadkevich |
| 2014/0336690 A1 | 11/2014 | Zhadkevich |

FOREIGN PATENT DOCUMENTS

| | | |
|---|---|---|
| EP | 2 260 776 A1 | 12/2010 |
| EP | 2 682 1154 A1 | 1/2014 |
| WO | WO 09/36028 | 7/1990 |
| WO | WO 98/47558 | 6/1998 |
| WO | WO 00/32266 A1 | 6/2000 |
| WO | WO 01/13983 A2 | 3/2001 |
| WO | WO 2010/081025 A1 | 7/2010 |
| WO | WO 2011/017103 A2 | 2/2011 |
| WO | WO 2011/068946 A1 | 2/2011 |
| WO | WO 2012/083227 A1 | 6/2012 |

OTHER PUBLICATIONS

Joe Elbery; "Swan Ganz Physiology"; You Tube video retrieved from https://www.youtube.com/watch?v=7putxZN7ij4; Jan. 21, 2012; copyright 2012; published by Edwards Lifescience, Irvine, California, USA; (2 pages screen shot included).

Various Anonymous Authors; "Circle of Willis"; Wikipedia article retrieved from https://en.wikipedia.org/wiki/Circle_of_Willis; retrieved on Nov. 8, 2016; pp. 1-4; copyright 2016 Wikipedia Foundaton Inc.; San Francisco; California; USA; copy encloded (4 pages).

European Patent Office; Extended European Search Report; European Application No. 13175517.5-1506; European Patent Office; pp. 1-10; publisher European Patent Office; Published Berlin Germany; copyright and dated Oct. 7, 2013; copy in parent application (9 pages).

United States Patent Office, Office Action; U.S. Appl. No. 15/333,076; United States Patent Office; pp. 1-15, publisher United States Patent Office; Published Alexandria, Virginia, USA; copyright and dated Sep. 5, 2018; (15 pages).

* cited by examiner

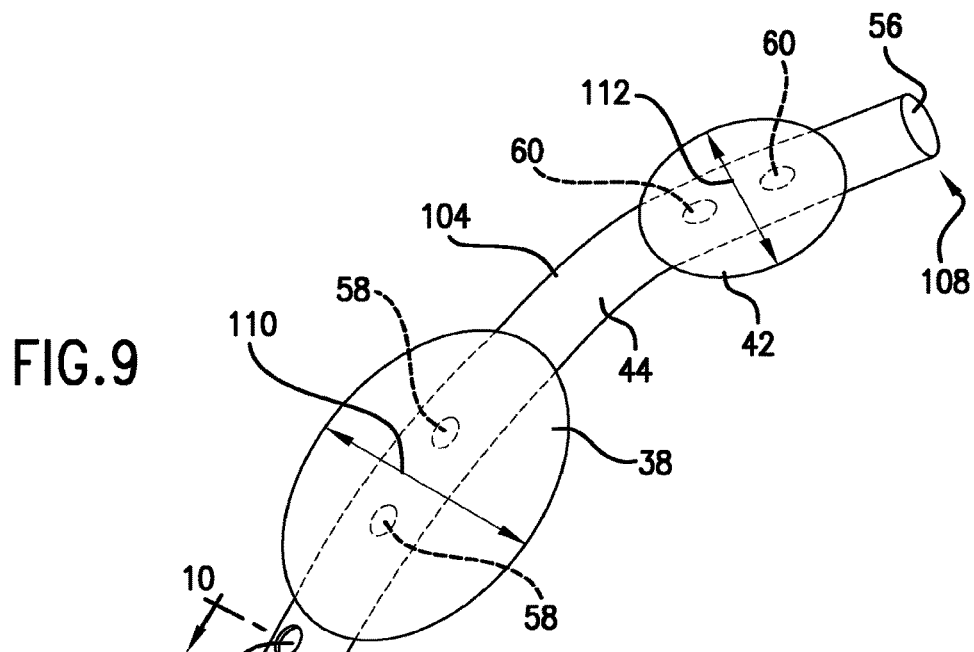
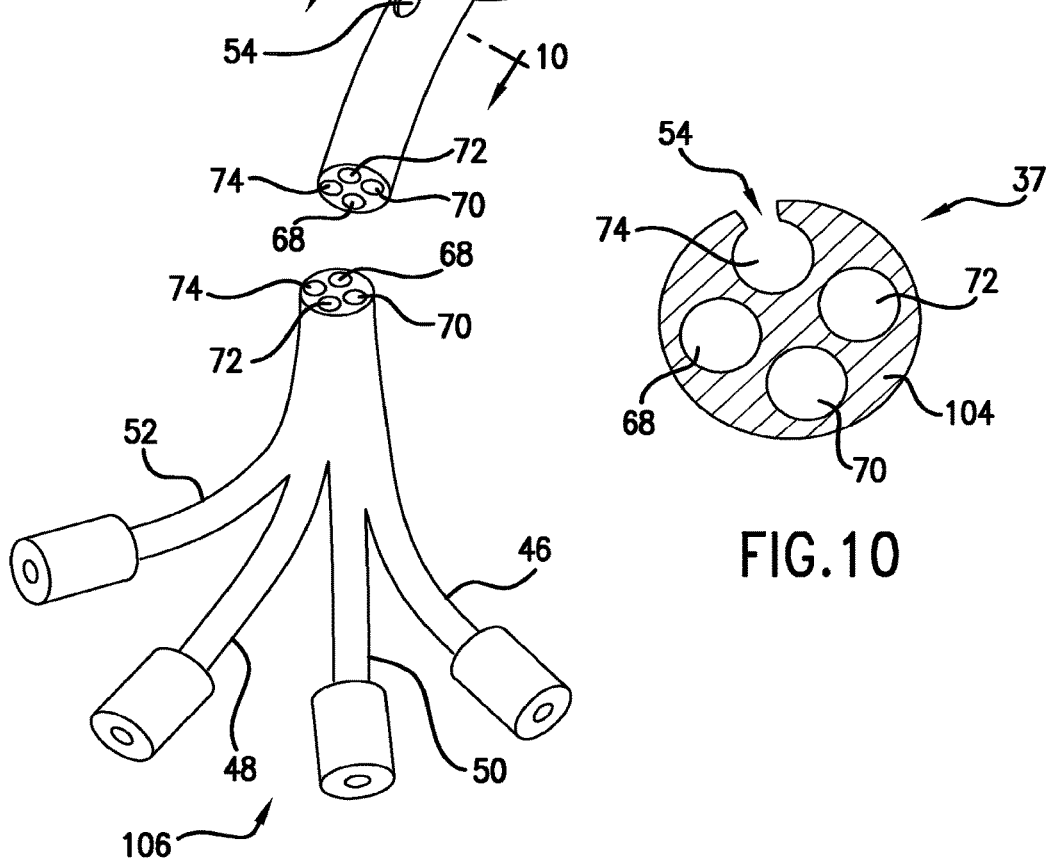
FIG.9
FIG.10

OCCLUDING CATHETER FOR PREVENTION OF STROKE

CROSS REFERENCE TO RELATED APPLICATIONS

This application is a divisional application of and claims the benefit of U.S. application Ser. No. 13/918,492 filed on Jun. 14, 2013 and entitled "Occluding Catheter and Method for Prevention of Stroke" that issued on Nov. 22, 2016 as U.S. Pat. No. 9,498,225. U.S. Pat. No. 9,498,225 claims the benefit of U.S. Application Ser. No. 61/668,980 filed on Jul. 6, 2012 and entitled, "Device and method of prevention of embolic stroke." U.S. Application Ser. No. 61/668,980, U.S. Application Ser. No. 61/668,980, and U.S. Pat. No. 9,498,225 are incorporated by reference herein in their entireties for all purposes.

FIELD OF THE INVENTION

The present invention relates generally to devices and methods for the prevention of stroke. More particularly, the present application involves an occluding catheter that has at least one balloon that is inserted into the circulatory system of the patient to block blood flow and hence emboli through the carotid arteries and if needed subclavian arteries during performance of an emboligenic procedure to prevent emboli from passing through the carotid arteries and subclavian arteries and causing stroke.

BACKGROUND

Intraoperative embolic stroke is one of the most dreadful complications of cardiac, aortic and vascular procedures, diagnosed in 1-22% of patients undergoing cardiovascular surgery. Even more frequently, in up to 70% of cases, patients undergoing heart, valve, coronary artery bypass and aortic surgery experience subclinical embolic events as recorded by transcranial Doppler and MRI. These embolic events lead to cognitive impairment and disability and have a significant impact on patients' recovery.

The main sources of cerebral emboli and stroke in this setting reside in the heart, heart valves, thoracic aorta, and great vessels when these structures are intervened thereon. Even simple cardiac catheterization with an endovascular catheter can induce microtrauma of the atherosclerotic thoracic aorta leading to formation of embolic particles with subsequent embolic brain injury ranging from latent ischemic foci to a massive or even fatal stroke.

Multiple devices are known that attempt to prevent embolization of the carotid arteries during endovascular and cardiac interventions. These anti-embolic devices, however, have not received wide acceptance in surgery of the heart, heart valves and thoracic aorta due to their complexity and invasive character with the risk of additional trauma to the inner vessel wall resulting in a high risk to benefit ratio. Known devices require insertion of additional hardware into the arterial system or aorta, a procedure that is known by itself to be associated with all classical risks of endovascular intervention, including aortic dissection, bleeding, thrombosis, and carotid cerebral embolization and stroke. One known intra-aortic filter device that is inserted into the ascending portion of the thoracic aorta via an aortic cannula to capture potential embolic material released from the heart and aortic wall during heart surgery was found to be quite difficult to implement and was reported to be associated with major trauma to aortic wall and acute aortic dissection.

Another such device for preventing emboli into the cerebral circulation includes a porous deflector/intra-aortic shield that captures or diverts potential emboli into the distal vasculature. A yet additional device has also been proposed for use during aortic valve surgery and is an intra-aortic filter catheter that captures emboli during this procedure. It has been established that intravascular filters are not able to capture emboli smaller than the pore size of the available devices (currently 60-140 µm) resulting in cerebral microembolization. Embolization may also occur due to poor apposition of the filter to the aortic or carotid arterial wall.

Furthermore, the placement of the filter by itself may produce cerebral emboli. For example, the mere passing of a guide wire into a carotid artery generates approximately 40,000 microemboli, with a significant percentage of small, less than 60 µm, particles that are not retained by standard filters. Therefore, in spite of multiple innovations in the field of anti-embolic devices, the problem of cerebral emboli and stroke during cardiovascular surgery is far from being resolved.

It is known to use balloon occlusion catheters for the prevention of embolic stroke. In this regard, the balloon occlusion catheter is placed inside of one of the carotid arteries when a procedure, for example carotid angioplasty and stenting, is conducted on the carotid artery in question. Although capable of preventing stroke when a single carotid artery is operated upon, this device cannot work to prevent stroke during procedures on the heart and aorta, endovascular or open, and cannot provide for bilateral occlusion. This device cannot simultaneously occlude both the left and right carotid arteries to prevent flow simultaneously through both of these arteries, and thus cannot prevent stroke should emboli flow into the non-blocked carotid artery.

Further, known endovascular carotid occluding devices require a guide wire to be inserted into the carotid arterial system. This procedure by itself is known to induce carotid trauma and cause the formation of cerebral emboli and resultant stroke. Still additionally, prior endovascular carotid occluding devices are not capable of reducing arterial flow through both right and left vertebral arteries, either at the same time or individually. This deficiency may allow emboli to enter vertebrobasilar circulation and cause stroke. As such, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 9 is a perspective view of the occluding catheter of FIG. 2 in an inflated state and with a section cut away to view interior portions.

FIG. 10 is a cross-sectional view taken along line 10-10 of FIG. 9.

Figure 1:
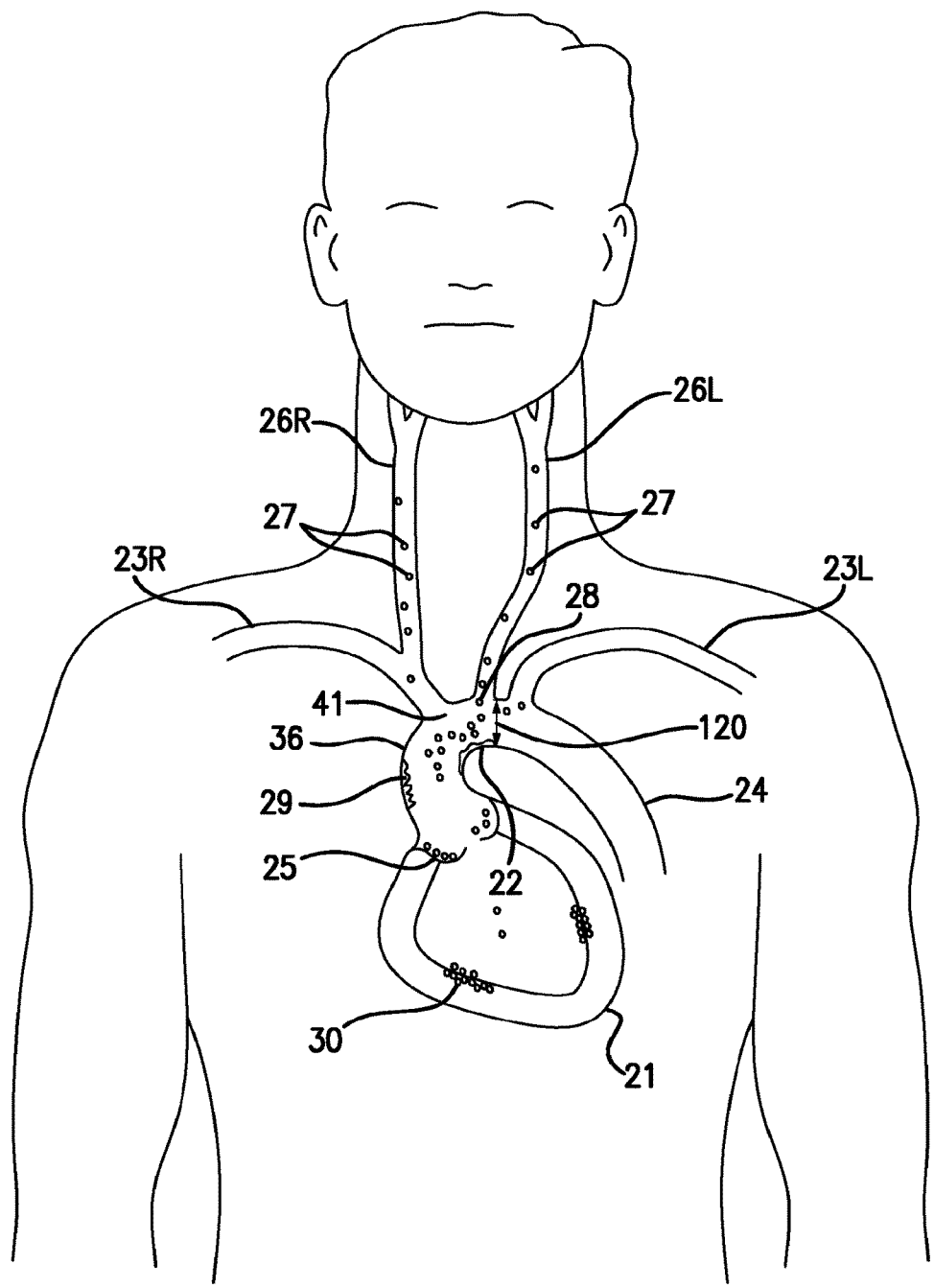
FIG. 1 is a front view of a patient with emboli in the heart and ascending thoracic aorta with subsequent propagation of emboli into both carotid arteries with the source of emboli being diseased aorta, aortic valve and the heart.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an occluding catheter 37 that may be introduced into the circulatory system of a patient in order to prevent emboli 28 from entering the carotid arteries 26R, 26L and causing stroke. The occluding catheter 37 may be arranged so that has one occluding balloon 38, or a pair of occluding balloons 38 and 42, or three or more occluding balloons in accordance with different exemplary embodiments. The occluding catheter 37 can be positioned within the circulatory system in a deflated state. When needed, the occluding catheter 37 can be inflated in order to block blood flow through the carotid arteries 26R, 26L and hence prevent emboli 28 from flowing through the carotid arteries 26R, 26L and into cerebral circulation. The occluding catheter 37 can be equipped with the capability of employing a guide wire 100 and with the ability to measure pressure downstream in one or more arteries of the patient to ensure proper blockage. If needed or desired, flow may be blocked through both vertebral arteries. An associated method for preventing emboli 28 from entering cerebral circulation is also provided.

With reference to FIG. 1, a front view of a patient is shown in which emboli 28 are transferred from the aortic arch 22 into the carotid arteries 26R, 26L. The emboli 27 that are present in the carotid arteries 26R, 26L can then be transferred into the cerebral circulation causing stroke of the patient. The emboli 27 may be fragments of atherosclerotic plaque 29 of the ascending aorta 36 that become dislodged during manipulation of the ascending thoracic aorta 36. Also shown in FIG. 1 is calcification of the aortic valve 25 and intracardiac emboli 30 of the heart 21 that can also be the origin of emboli 27 eventually present in the carotid arteries 26R, 26L. The intracardiac emboli 30 may include air, gas, thrombi and atherosclerotic materials. Although all of the various emboli in the heart 21, aortic arch 22, ascending aorta 36, and aortic valve 25 need not be present in all instances, they are all shown in FIG. 1 for sake of example. Trauma to the heart 21, aortic valve 25 and aortic structures during placement and removal of items such as aortic clamps and electrophysiological instruments, along with manipulations such as coronary artery bypass grafting, aortic and mitral valve replacement, catheter ablation, endovascular grafting of the aorta 22, balloon valvuloplasty percutaneous implantation of the aortic or mitrel valves, endovascular manipulations on the aorta 22, aortic branches and the heart 21 may give rise to the presence of emboli 27 in the carotid arteries 26R, 26L. Critical moments of the aforementioned procedures (for example during the aortic cross clamp manipulation, percutaneous aortic and mitral valvuloplasty or valve implantation, coronary interventions, endovascular grafting of the aorta 22 and its branches, and endovascular procedures on the aorta 22) may cause emboli 27 to form and cause stroke and are referred to as "embo-ligenic" events.

Figure 2:
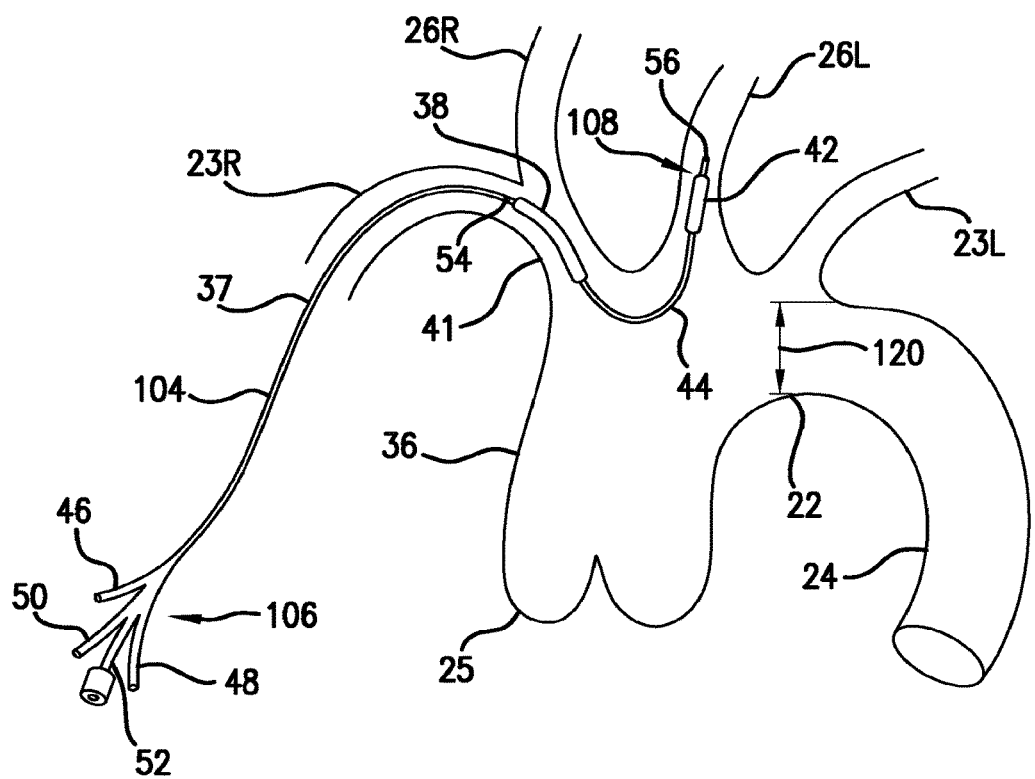
FIG. 2 is a front view of the patient with an occluding catheter in a deflated state positioned within the circulatory system of the patient.

FIG. 2 discloses an occluding catheter 37 positioned within the circulatory system of the patient. The occluding catheter 37 is introduced through a right subclavian artery 23R and has a shaft 104 with a proximal end 106 located outside of the patient, and a distal end 108 positioned within the left carotid artery 26L. The occluding catheter 37 has a proximal occluding balloon 38 located closer to the health care provider and thus closer to the proximal end 106 than a distal occluding balloon 42 which is farther away from the health care provider and thus closer to the distal end 108. The proximal occluding balloon 38 may be located within an innominate artery 41 of the patient. The occluding catheter 37 can be arranged as shown in FIG. 2 so that no portion of it is located within the right carotid artery 26R. In other exemplary embodiments, some portion of the occluding catheter 37 may be located within the right carotid artery 26R. A segment 44 of the shaft 104 that is located between the proximal and distal occluding balloons 38, 42 may be located in the aortic arch 22.

The occluding catheter 37 may be inserted into the right subclavian artery 23R via right radial, brachial, axillary or subclavian artery approach and can be advanced under fluoroscopic and arterial blood pressure guidance into the innominate artery 41, aortic arch 22 and finally into the left carotid artery 26L. The ideal position of the proximal tip of the distal occluding balloon 42 may be in the proximal segment of the left carotid artery 26L, whereas the proximal occluding balloon 38 may reach the level of the innominate artery 41.

The insertion of the occluding catheter 37 may be performed when both the proximal 38 and distal 42 occluding balloons are deflated. However, once the distal occluding balloon 42 reaches the level of the aortic arch 22 it can be inflated to facilitate its advancement into the left carotid artery 26L. The inflated distal occluding balloon 42 is thus naturally propelled forward into the left carotid artery 26L by arterial blood flow. The adequacy of the position of the distal occluding balloon 42 is confirmed with fluoroscopy and, if desired, by appearance of the dampened arterial pressure recorded from the end pressure measurement channel 70 through the end pressure measurement port 50 with its distal tip opening 56 located distal from the tip of the distal occluding balloon 42 downstream from the area of occlusion of the left carotid artery 26L.

Once an adequate position of the distal occluding balloon 42 in the left carotid artery 26L is achieved it may be deflated. A normal arterial blood pressure waveform as recorded from the distal tip opening 56 should reappear to confirm adequate perfusion via the left carotid artery 26L.

Correct placement of the distal occluding balloon 42 within the left carotid artery 26L may result in correct placement of the proximal occluding balloon 38 within the innominate artery 41. This is achieved by choosing an occluding catheter 37 with the longitudinal length of segment 44 between proximal and distal occluding balloons 38, 42 to be slightly larger than the distance between the left carotid artery 26L and innominate artery 41 as estimated by preoperative CT scan. According to some measurements, an optimal length of segment 44 should be 2-6 cm longer than the distance between the innominate artery 41 and the left carotid artery 26L to allow for a smooth turn of the interballoon portion of the occluding catheter 37 within the aortic arch 22. Considering the fact that the average distance between the orifices of the innominate artery 41 and left carotid artery 26L in the normal aortic arch 22 configuration is from 0.5-1.0 cm, the length of segment 44 between the distal and proximal occluding balloons 38 and 42 should lie within the range between 3 and 8 cm. Therefore, in practice several different sizes of the occluding catheter 37 can be constructed where the length of the segment 44 between the proximal 38 and distal 42 occluding balloons vary from 3 to 12 cm. The diameter, volume and length of the occluding balloons 38, 42 may also vary according to the patient's anatomy with the proximal occluding balloon 38 being 50-100% longer and larger than its distal 42 counterpart. The length of segment 44 may be selected so that the proximal occluding balloon 38 is located within the innominate artery 41 at the same time that the distal occluding balloon 42 is located within the left carotid artery 26L.

The next step in the method of using the occluding catheter 37 may be the inflation of the proximal occluding balloon 38 in the lumen of the innominate artery 41 and the recording of post-occlusion pressure in the distal innominate artery 41. This pressure may be recorded via an opening 54 of the shaft 104 located downstream from the proximal occluding balloon 38 in the direction of arterial blood flow. An intermediate pressure measurement channel 74 is in communication with the opening 54 and with an intermediate pressure measurement port 52 at the proximal end 106. This port 52 can be used to confirm an adequate position of the proximal occluding balloon 38 by the appearance of the dampened waveform. Once the pressure measurement indicates that the proximal occluding balloon 38 is properly positioned, the proximal occluding balloon 38 can be deflated and the occluding catheter 37 is considered ready for use. The interruption of carotid flow or pulse may be assessed by angiography, carotid Doppler, or arterial pressure and waveform patterns distal to the level of occlusion in accordance with certain exemplary embodiments. In addition, percutaneous cerebral oximetery, electroencephalography and transcranial Doppler monitoring can be applied. In other arrangements, it may not be the case that this monitoring is applied in order to confirm positioning of the proximal and distal occluding balloons 38, 42.

Figure 3:
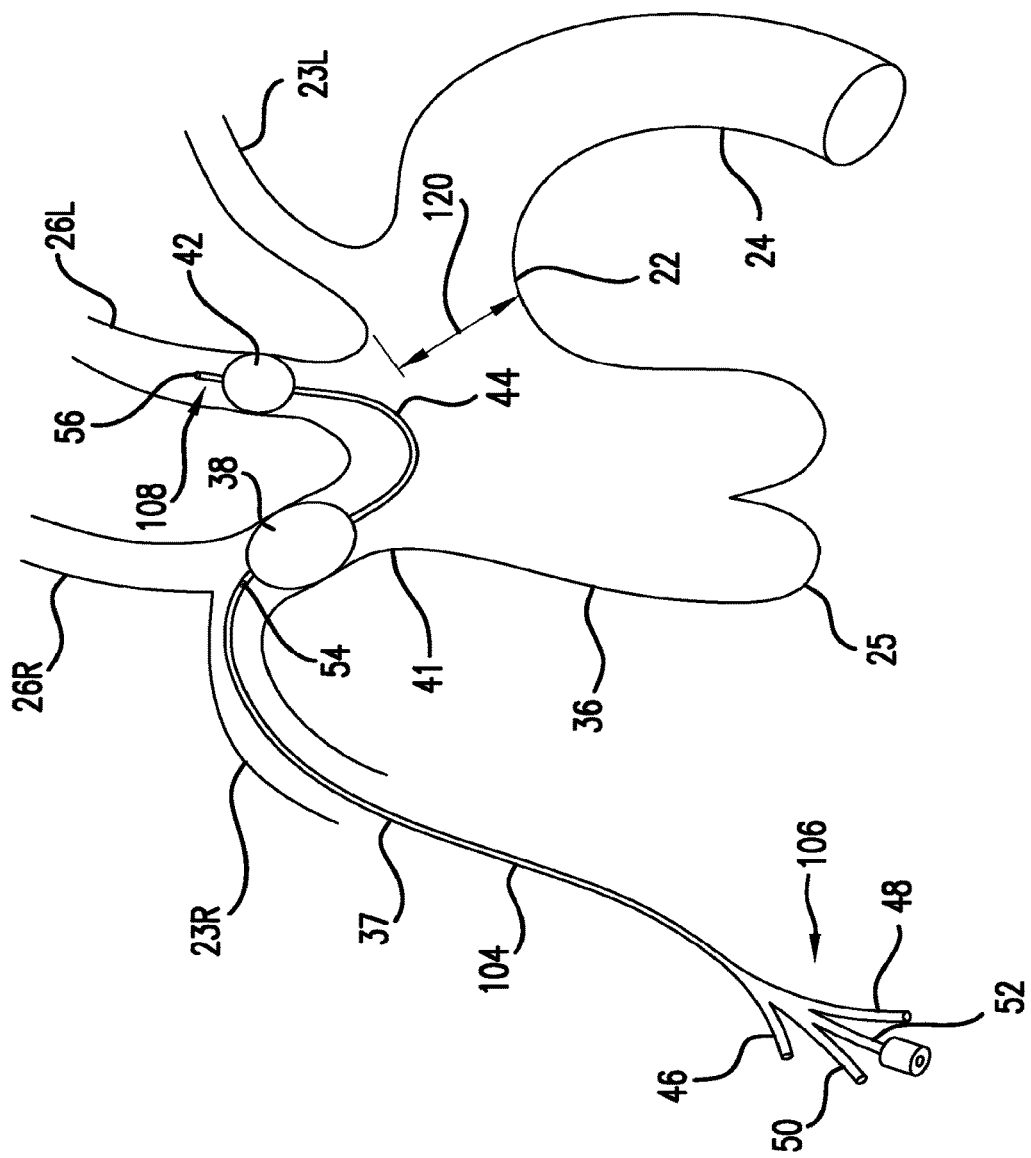
FIG. 3 is a front view of the patient of FIG. 2 with the occluding catheter in an inflated state.

The proximal and distal occluding balloons 38, 42 may be inflated such that they are both inflated at the same time as shown with reference to FIG. 3. Simultaneous inflation may lead to temporary interruption of the carotid arterial flow, preventing all potential emboli 28, released due to manipulations on atherosclerotic calcified plaques 29 of the ascending aorta 36 (or from other such emboligenic events) from entering the cerebral circulation, and diverging them downstream from the cerebral circulation into the descending aorta 24, thus protecting the patient from embolic stroke. The occluding balloons 38, 42 may be inflated to such a pressure and be of such a resiliency that they completely block any blood flow past them and through the particular artery or arteries into which they are positioned. However, it is to be understood that other arrangements are possible in which some amount of blood may flow past the proximal occluding balloon 38 and/or the distal occluding balloon 42.

Figure 4:
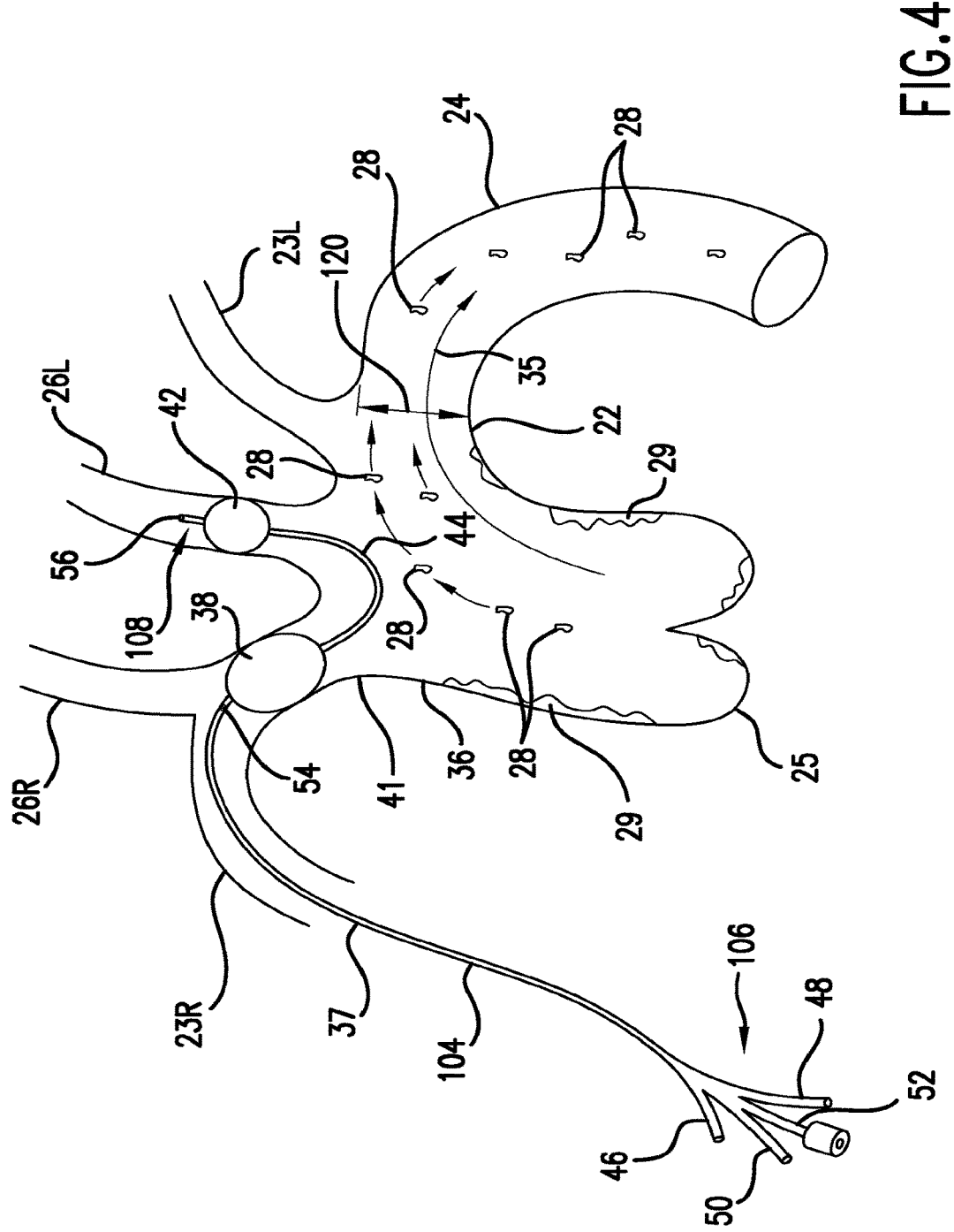
FIG. 4 is a front view of the patient of FIG. 3 that shows the divergence of emboli.
Figure 5:
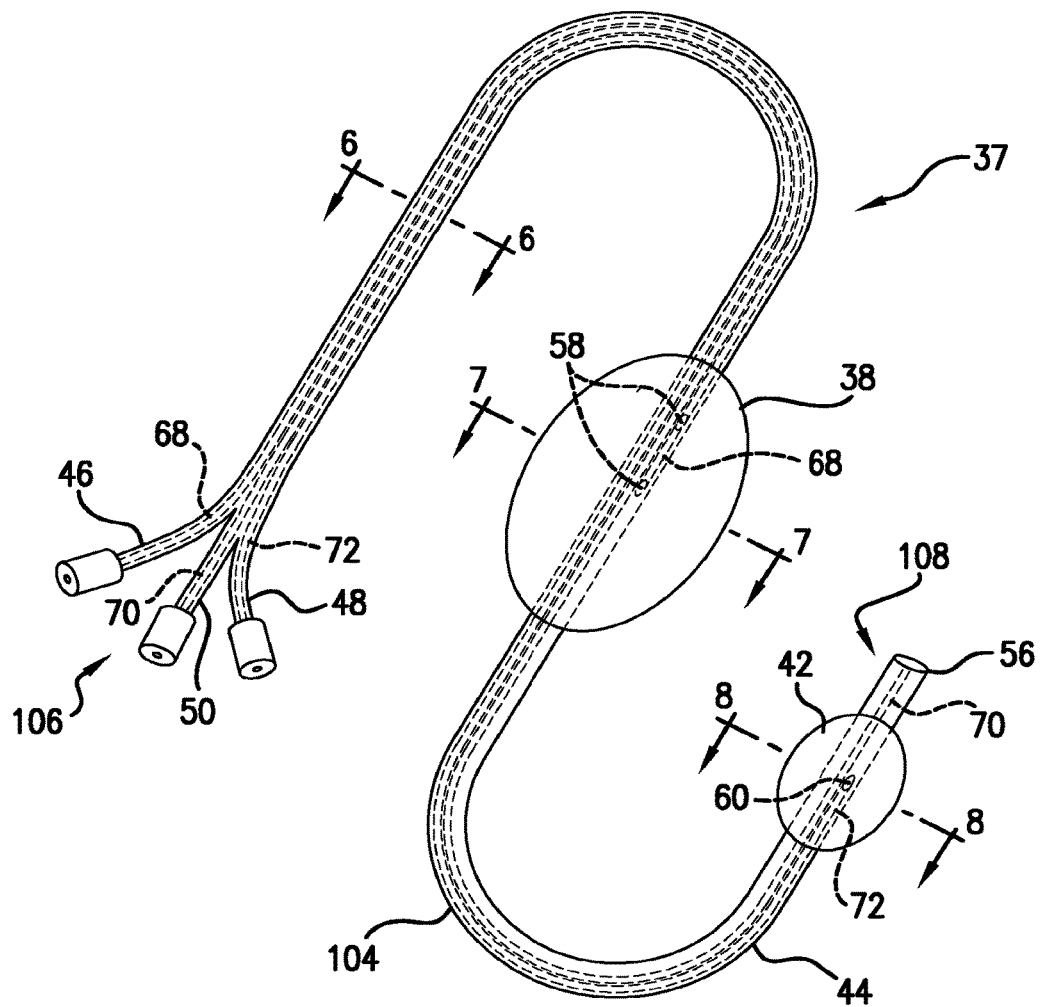
FIG. 5 is a front view of an occluding catheter in accordance with one exemplary embodiment in an inflated state.
Figure 6:
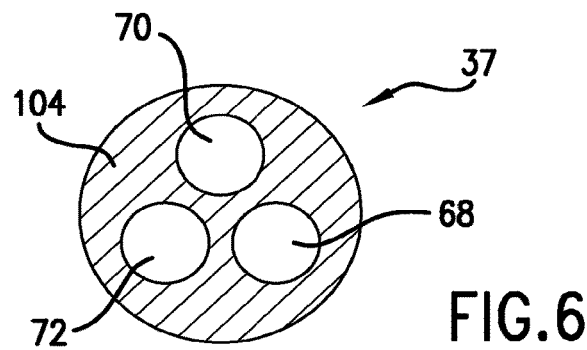
FIG. 6 is a cross-sectional view taken along line 6-6 of FIG. 5.
Figure 7:
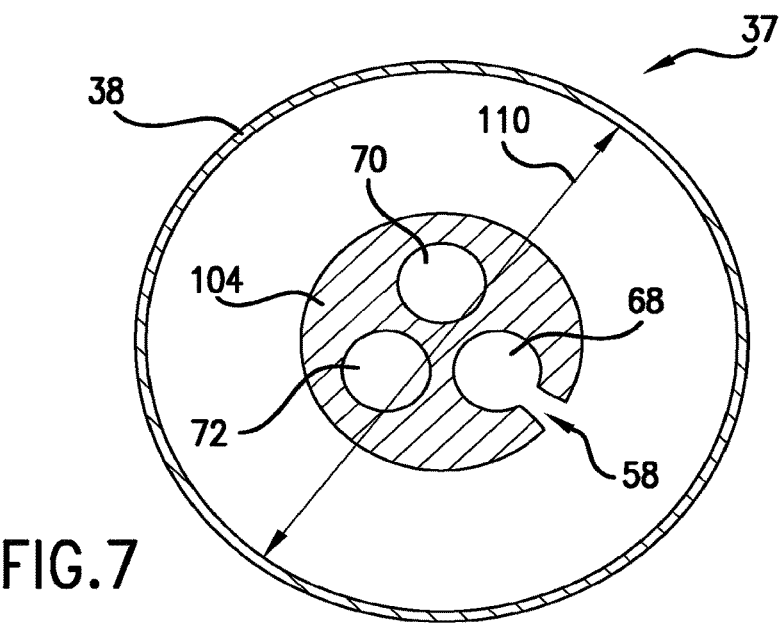
FIG. 7 is a cross-sectional view taken along line 7-7 of FIG. 5.
Figure 8:
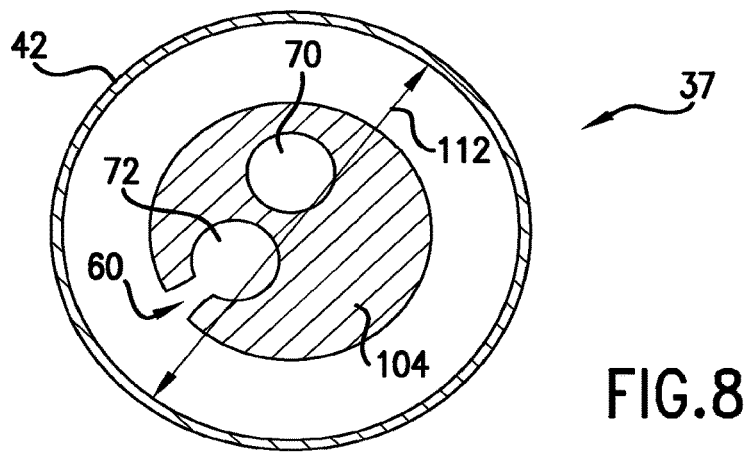
FIG. 8 is a cross-sectional view taken along line 8-8 of FIG. 5.

FIG. 4 illustrates the flow of blood in the circulatory system upon inflation of the proximal and distal occluding balloons 38 and 42. Temporary interruption of flow at the level of the proximal carotid arteries 26R, 26L leads to divergence of blood flow 35 carrying all potential cerebral emboli 28 into the descending aorta 24. Emboli 28 diverted from cerebral circulation move through the descending aorta 24. The proximal occluding balloon 38 may completely block the innominate artery 41 so that no blood flow or emboli 28 may be transferred through the right carotid artery 26L and the right subclavian artery 23R. The position of the proximal occluding balloon 38 can be made so that it is right at the bifurcation of the innominate artery 41 in order to completely occlude the orifice of the right carotid 26R and right subclavian 23R arteries at the same time.

Both distal and proximal occluding balloons 38, 42 are inflated just before proceeding with the part of the procedure prone to generate cerebral emboli 27. This may be the placement or removal of an aortic cross clamp, implantation of valves, endovascular grafts and stents, or other procedures outlined above. The balloon pressure required to completely interrupt flow in carotid arteries 26R, 26L at this point of intervention is usually significantly less and rarely exceed 50 mm of mercury. This consideration is based on the fact that the physician may bring the systemic perfusion pressure of the patient to minimal levels at this particular time of the procedure that involves the emboligenic event. Therefore, the occluding balloon 38, 42 pressure required to occlude carotid arteries 26R, 16L at this short period of time can be significantly lower and less damaging to the carotid arterial walls 26R, 26L.

Inflation of the occluding balloons 38, 42 can be such that they are inflated to a pressure exceeding the patient's systemic pressure by 10-20 mm Hg or more just before proceeding with the emboligenic part of the procedure. Adequate occlusion of the carotid arteries 26R and 26L will lead to a known phenomenon of a temporary reduction of flow through vertebral arteries leading to additional divergence of blood and emboli 28 away from both vertebral arteries. This will decrease the risk of stroke in vertebrobasilar circulation. Insertion of the occluding catheter 37 through the right side and inflation of the proximal occluding balloon 38 at the level of the innominate artery 41 may preclude entrance of emboli 28 into the right subclavian artery 23R and right vertebral arterial system. Insertion of the occluding catheter 37 through the left side of the patient may cause the proximal occluding balloon 38 to be at the level of the left subclavian artery 23L to preclude entrance of emboli into the left subclavian artery 23L and left vertebral arteries, and the distal balloon 32 to be at the level of the innominate artery 41, to preclude entrance of emboli into the right carotid 26R, right subclavian 23R and right vertebral arteries, further reducing the risk of embolic stroke.

The distal and proximal occluding balloons 38, 42 may be deflated 30-90 seconds after this part of the procedure is completed to achieve complete washout of all potential emboli 28 into the descending aorta 24 and distal vasculature, while avoiding migration of emboli 28 into the carotid arteries 26R and 26L. This timing, however, can be either shortened or extended depending on multiple factors that comprise the timing of embolic events, their intensity and the degree of patient's tolerance to transient interruption of cerebral flow such as the degree of hypothermia and the condition of the collateral cerebral flow as measured by EEG, transcranial Doppler, or other means.

The length of most manipulations associated with a transgression of emboli into cerebral circulation rarely exceed 1-2 minutes. Temporary interruption of the carotid flow for this period of time, plus 0.5-1.5 min to allow for complete washout of emboli 28 from the aorta 22 is completely safe and feasible.

Partial deflation of the balloons 38, 42 may provide necessary blood flow to the brain while still decreasing the degree of cerebral embolization. The technology will allow one to extend the length of cerebral protection from embolic stroke while assuring cerebral perfusion.

Once the emboligenic procedure is completed both occluding balloons 38 and 42 may be deflated. Optionally, repeating the whole process of cerebral protection may be conducted if desired once a 5-10 min period of cerebral reperfusion is reached. The procedure can be repeated at any time of surgery and on multiple occasions when the emboligenic intervention is anticipated. Upon completion of the main surgical procedure, the occluding catheter 37 can be completely removed or pulled back completely into the right subclavian artery 23R for later removal.

FIGS. 5-8 illustrate an exemplary embodiment of the occluding catheter 37 as being a 3-lumen, 2-balloon catheter 37. The occluding catheter 37 includes a shaft 104 that may have an outer circumference that is circular in cross-sectional shape. However, other cross-sectional shapes of the outer circumference are possible in accordance with other exemplary embodiments. Ports 46, 48 and 50 may have openings at their extreme proximal ends to allow for communication with their respective channels 68, 70, 72 and can have fittings configure to receive inflation syringes, pressure measurement devices, guide wires 100 or other components. Channels 68, 70, and 72 have circular cross-sectional shapes and are all the same diameter. However, in other arrangements the cross-sectional shapes may be different and their diameters can be variously sized such that they are not the same size as one another.

The channels 68, 70 and 72 are not in fluid communication with one another. The proximal and distal occluding balloons 38, 42 may be inflated separately from one another such that one is inflated before another one, or such that both inflate simultaneously. Pressure of inflation supplied by a pressure supply 126 may be to a degree greater than the patient's systemic arterial pressure. The pressure inside the occluding balloons 38, 42 may exceed only minimally the patient's systemic and carotid arterial 26R, 26L pressures with the goal to achieve complete interruption of the antegrade carotid flow without undue trauma to these vessels 26R, 26L.

Proximal occluding balloon inflation port 46 is in fluid communication with the proximal occluding balloon channel 68. The channel 68 may terminate at the proximal occluding balloon 38 and may not extend past the proximal occluding balloon 38 in the distal direction. One or more openings 58 may extend through the shaft 104 in order to place the channel 68 into fluid communication with the interior of the proximal occluding balloon 38. Fluid pressure supplied by a syringe or other source may be introduced through port 46, channel 68 and out of opening 58 in order to inflate the proximal occluding balloon 38 to its inflated state.

The proximal occluding balloon 38 may be connected on its distal and proximal ends to the shaft 104 and inflation pressure will cause the proximal occluding balloon 38 to expand so as to have a circular cross-sectional shape. The proximal occluding balloon 38 may have other cross-sectional shapes in other exemplary embodiments such as oval or elliptical. The occluding balloon 38 may be variously shaped and sized in accordance with different exemplary embodiments. The proximal occluding balloon 38 may be coaxial with the shaft 104. In accordance with various embodiments, the proximal occluding balloon 38 may be coaxial with the channel 70, 72 or 68. In other embodiments the proximal occluding balloon 38 is not coaxial with the shaft 104 or any of the channels 70, 72 or 68.

The shaft 104 continues in the distal direction past the proximal occluding balloon 38 but only channels 70 and 72 are present past the proximal occluding balloon 38. The distal occluding balloon 42 is located at the distal end 108 of the shaft such that a segment 44 of the shaft 104 is present between the occluding balloons 38, 42 to space them from one another. The distal occluding balloon channel 72 extends from the distal occluding balloon inflation port 48 and terminates at an opening 60 of shaft 104. The distal occluding balloon 42 is attached at its proximal and distal ends to the shaft 104 and is inflated via pressure supplied through port 48, channel 72 and out of opening 60. A single opening 60 may be present, or a plurality of openings 60 may be present through which pressure can be supplied to inflate the distal occluding balloon 42. The distal occluding balloon 42 may have a circular cross-sectional shape, although other cross-sectional shapes are possible in other exemplary embodiments. The longitudinal length of the distal occluding balloon 42 may be less than that of the proximal occluding balloon 38. However, their longitudinal lengths may be the same in other arrangements, or in yet further designs the longitudinal length of the proximal occluding balloon 38 is less than the longitudinal length of the distal occluding balloon 42. The distal occluding balloon 42 may be coaxial with the shaft 104 in certain arrangements, and in other arrangements may be coaxial with channels 70 or 72. In yet other exemplary embodiments, the distal occluding balloon 42 is not coaxial with shaft 104 and is not coaxial with channels 70 or 72.

The diameter 112 of the distal occluding balloon 42 is less than the diameter 110 of the proximal occluding balloon 38. In other exemplary embodiments diameter 110 may be less than diameter 112, or the diameters 110 and 112 may be equal to one another. The diameters 110 and 112 may be the same along the entire longitudinal lengths of the occluding balloons 38, 42, or the diameters 110 and 112 may be different at different points along the longitudinal lengths of the occluding balloons 110 and 112. The diameters 110 and 112 and cross-sectional shapes of the proximal and distal occluding balloons 38, 42 are described when outside of the body of the patient.

The distal occluding balloon channel 72 may terminate proximal to the distal end of the distal occluding balloon 42. Only the end pressure measurement channel 70 may extend distally beyond the distal occluding balloon 42. The distal tip of the shaft 104 terminates at a distal tip opening 56 at its terminal distal end. The shaft 104 extends beyond the distal occluding balloon 42, but in other arrangements, the distal occluding balloon 42 in the inflated state may extend beyond the terminal distal end of the shaft 104 in the distal direction. The end pressure measurement port 50 can be in communication with the end pressure measurement channel 70 that in turn terminates at the distal tip opening 56. The channel 70 in other arrangements may be in fluid communication with one or both channels 68 and 72. Likewise, in yet other exemplary embodiments, channel 70 is not in fluid communication with channels 68 and 72, but channels 68 and 72 are in fluid communication with one another so that the proximal and distal occluding balloons 38, 42 inflate and deflate with one another. Distal tip opening 56 may be used for pressure measurements distal to the distal occluding balloon 42.

FIGS. 9 and 10 illustrate an alternative exemplary embodiment of the occluding catheter 37 that is a four-channel version of the occluding catheter 37. Intermediate pressure measurement channel 74 extends from an intermediate pressure measurement port 52 to an opening 54 of the shaft 104. Opening 54 is located proximal to the proximal occluding balloon 38. The intermediate pressure measurement channel 74 is not in fluid communication with the other channels 68, 70 and 72 of the occluding catheter 37. The intermediate pressure measurement channel 74 may terminate proximal to the proximal occluding balloon 38. The other components of the occluding catheter 37 are the same as described above and their description need not be repeated. A manometer may be connected to the intermediate pressure measurement port 52 to allow recording of blood pressure from the opening 54. If the proximal occluding balloon 38 is located within the innominate artery 41, the opening 54 may be used to detect the dampening of the arterial pressure in the innominate 41 and right carotid artery 26R, after proximal occluding balloon 38 inflation, confirming adequacy of the flow interruption to the right carotid 26R and subclavian arteries 23R.

Figure 11:
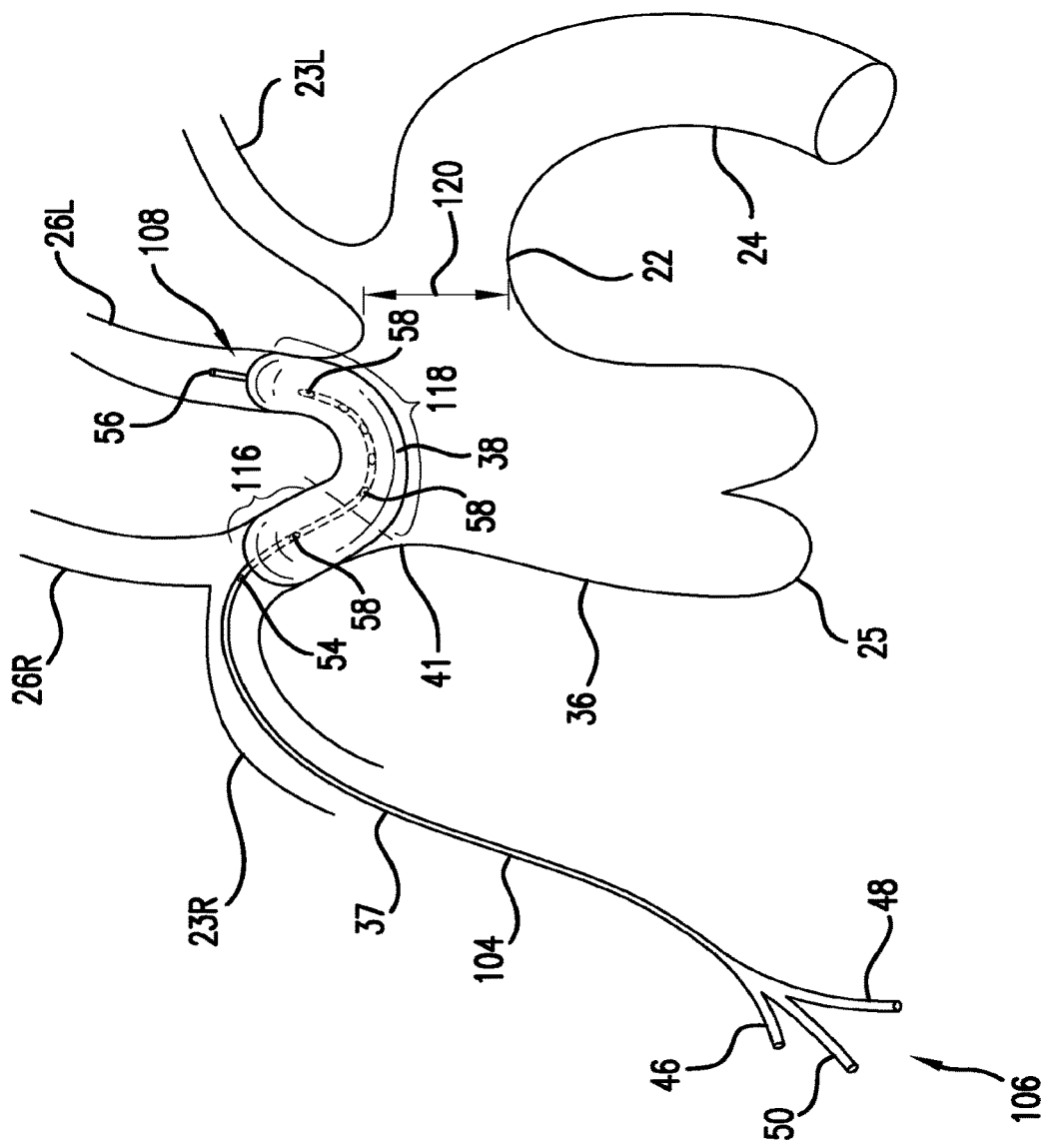
FIG. 11 is a front view of the patient with an inflated occluding catheter in accordance with another exemplary embodiment.

In another embodiment bilateral carotid 23R and 23L flow interruption can be achieved by creating a single occluding balloon 38. FIG. 11 shows one exemplary embodiment with a single occluding balloon 38. The occluding balloon 38 may extend throughout the whole distance between the bifurcation of the innominate artery 41 and the main trunk of the left carotid artery 26L. The single occluding balloon 38 may be longer than both the proximal occluding balloon 38 and distal occluding balloon 42 combined (as described in previous exemplary embodiments), with its length being in the range between 6 and 14 cm. When described as a single occluding balloon 38, it is to be understood that complete blockage of flow through the right and left carotid arteries 26R and 26L may be achieved by the single occluding balloon 38 without the use of any other occluding balloons, or without even the presence of another occluding balloon 38 carried by the occluding catheter 37.

The occluding balloon 38 may be constructed so that it has a proximal portion 116, designated to occlude the innominate artery 41, which is larger than a distal portion 118 of the occluding balloon 38 to assure adequate occlusion of the innominate artery 41. Generally, the innominate artery 41 is at least twice as large as the left carotid artery 26L. The single occluding balloon 38 may thus have a proximal portion 118 with a larger diameter than the diameter of the distal portion 118 of the single occluding balloon 38. These differences in diameters/sizes would be present when the single occluding balloon 38 is inflated without being inside of the patient. The other option involves the single occluding balloon 38 being a large volume, highly compliant occluding balloon that does not have any disparity in the diameters/size of the proximal portion 116 and distal portion 118 when inflated and not inside of the patient. Once inflated inside of the patient and presented with arteries of different sizes, the proximal and distal portions 116, 118 of the highly compliant occluding balloon 38 expand as necessary for complete occlusion of arteries 41 and 26L at minimal pressures and without significant compression of the arterial walls 41, 26L. The single occluding balloon 38 thus expands as necessary to fill the space required for occlusion as it is a very flexible member in construction.

Figure 12:
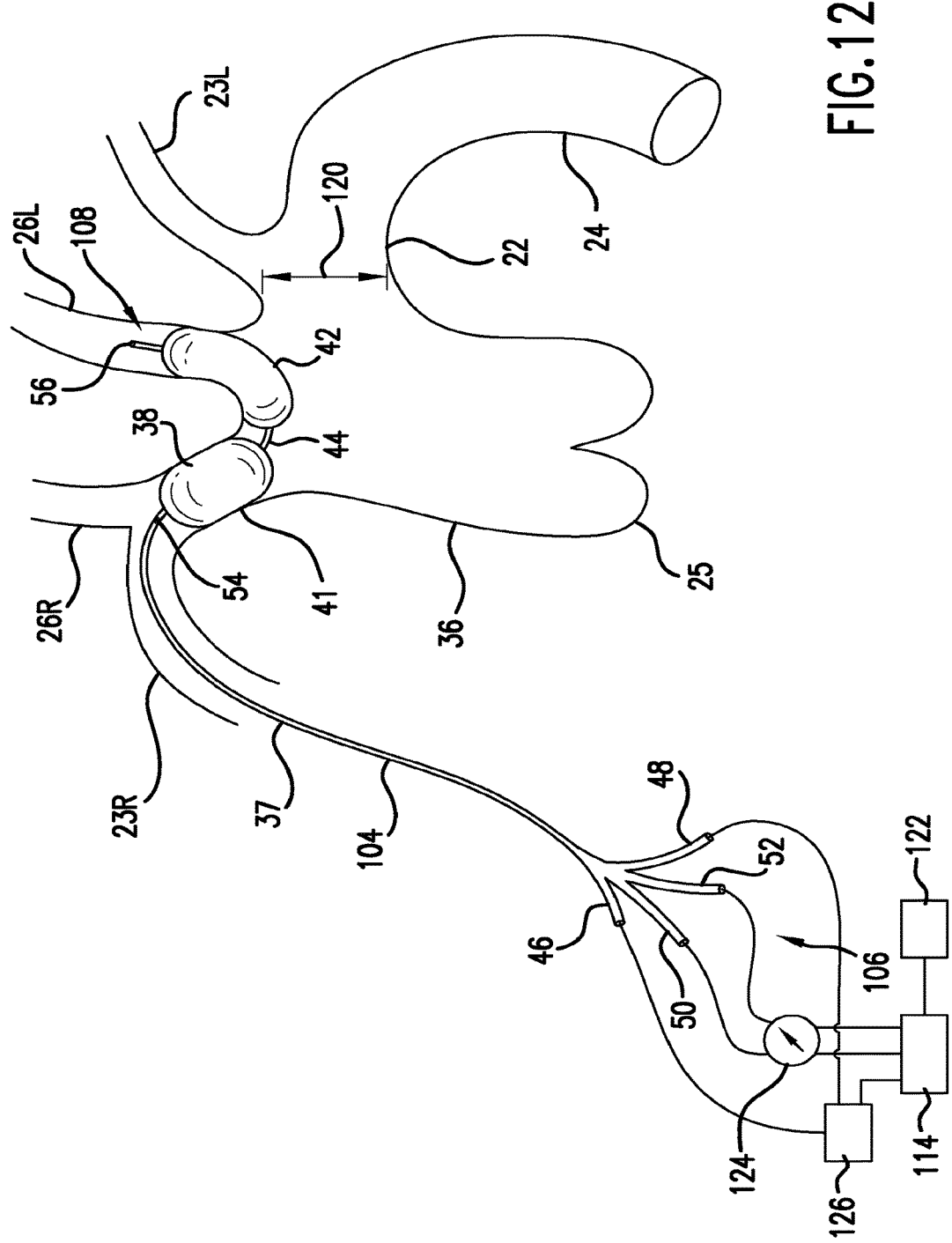
FIG. 12 is a front view of the patient with an inflated occluding catheter and an alarm system in accordance with a further exemplary embodiment.

In order to facilitate the advancement of the occluding catheter 37 in patients with difficult anatomy, a guide wire 100 may be used in one of the channels 70 or 74. With reference to FIG. 12, the guide wire 100 need not be used. Here, the shaft 104 is highly compliant and there is a narrow waist that makes up segment 44. The occluding catheter 37 includes a pair of occluding balloons 38, 42 and segment 44 in the middle of these occluding balloons 38, 42 improves flexibility of the occluding catheter 37. As previously described, separate occluding balloon channels 68 and 72 can be used for separate inflation of the proximal and distal occluding balloons 38 and 42. This allows for selective control of the occlusion of the left carotid artery 26L and innominate arteries 41.

The pair of occluding balloons 38, 42 in FIG. 12 may be rearranged so that they are only a single occluding balloon 38. In this regard, the single occluding balloon 38 will have a proximal portion 116 and a distal portion 118 separated by one another by segment 44 that is not capable of being inflated. A single occluding balloon channel 68 can be used to inflate both the proximal and distal portions 116, 118. Although a single occluding balloon 38 is present, it is divided into two or more portions via uninflated segments such as segment 44 or by various other bands or waists that effect division. Segment 44, when effecting separation of proximal and distal portions 116, 118, achieves better flexibility of the occluding catheter 37 at the level between the two portions 116, 118. This option may allow for an easier passage of the occluding catheter 37 in case of a sharp angle between the innominate artery 41 and left carotid artery 26L. If a pair of occluding balloons 38, 42 are employed the same goal may be achieved by the segment 44. Measurement of arterial pressure and assessing the pressure waveform via the openings 54, 56 before and after inflation will allow confirmation of the adequacy of the flow interruption in the carotid arteries 26L and 26R.

A manometer 124 may be in communication with the end pressure measurement port 50 and the intermediate pressure measurement port 52 to measure pressures at the opening of the shaft 54 (downstream from the proximal occluding balloon 38 in the innominate artery 41 or right subclavian artery 23R) and at the distal tip opening of the shaft 56 (downstream from the distal occluding balloon 42 in the left carotid artery 26L). A pressure supply 126 is in communication with the proximal occluding balloon inflation port 46 and the distal occluding balloon inflation port 48 to provide inflation pressure for the occluding catheter 37. An alarm system 114 is in communication with the pressure supply 126 and manometer 124. Should the physician or physician's assistant forget to deflate the occluding balloons 38, 42 in a timely fashion, an alarm would go off and the occluding balloons 38, 42 would deflate spontaneously to avoid undue interruption of the cerebral flow. The alarm could be also triggered by the occurrence of emboli 27 detected by transcranial Doppler 122 (also in communication with the alarm system 114) or any other means, thus indicating an urgent need for temporary occlusion of the cerebral flow. Here, the alarm system 114 will cause inflation of the occluding balloons 38, 42. The alarm system 114 along with deflation or inflation of the occluding balloons 38, 42 could be overridden by the physician when clinically indicated.

Figure 13:
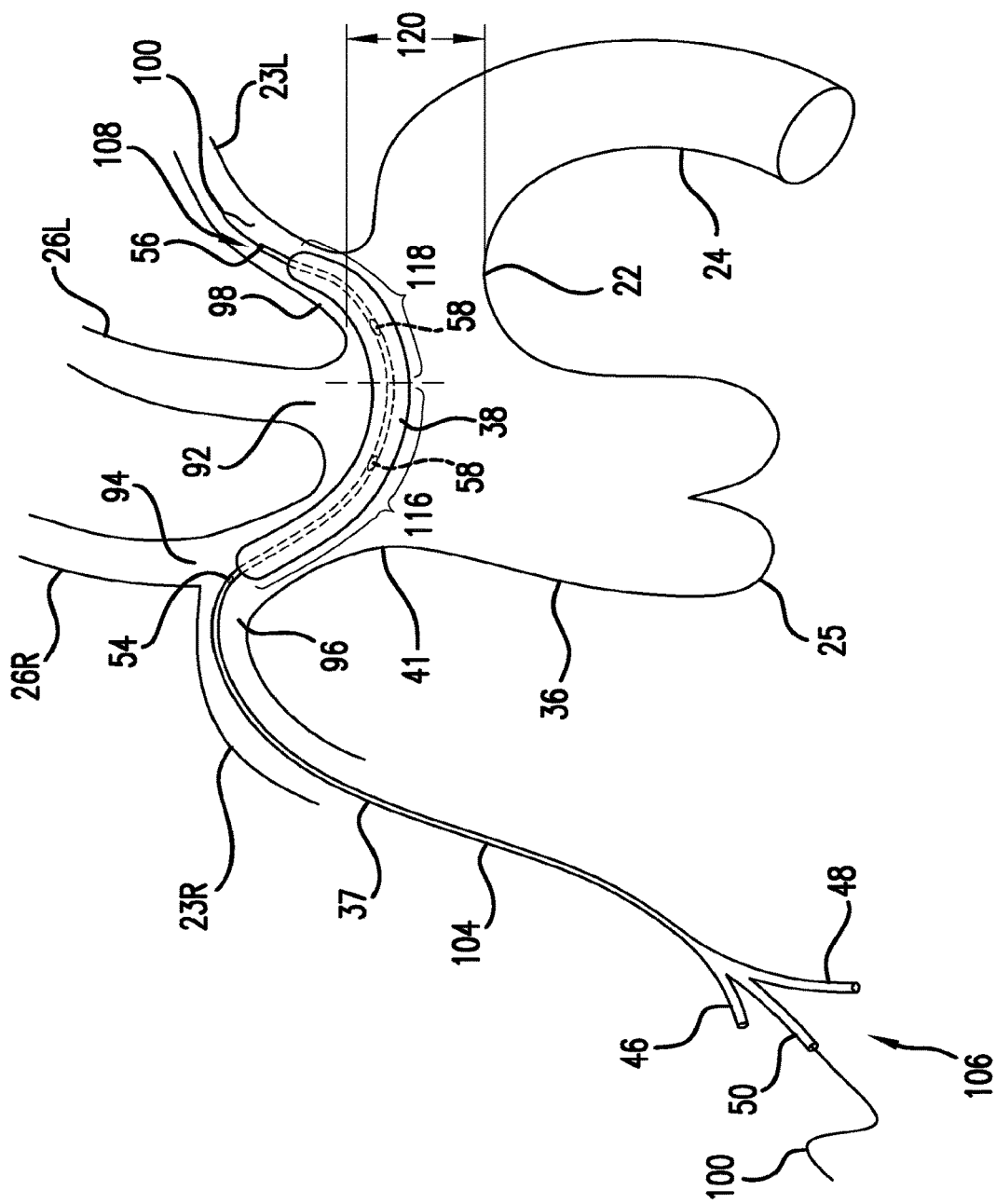
FIG. 13 is a front view of the patient with a deflated occluding catheter introduced through the arteries of the right arm in accordance with another exemplary embodiment.
Figure 14:
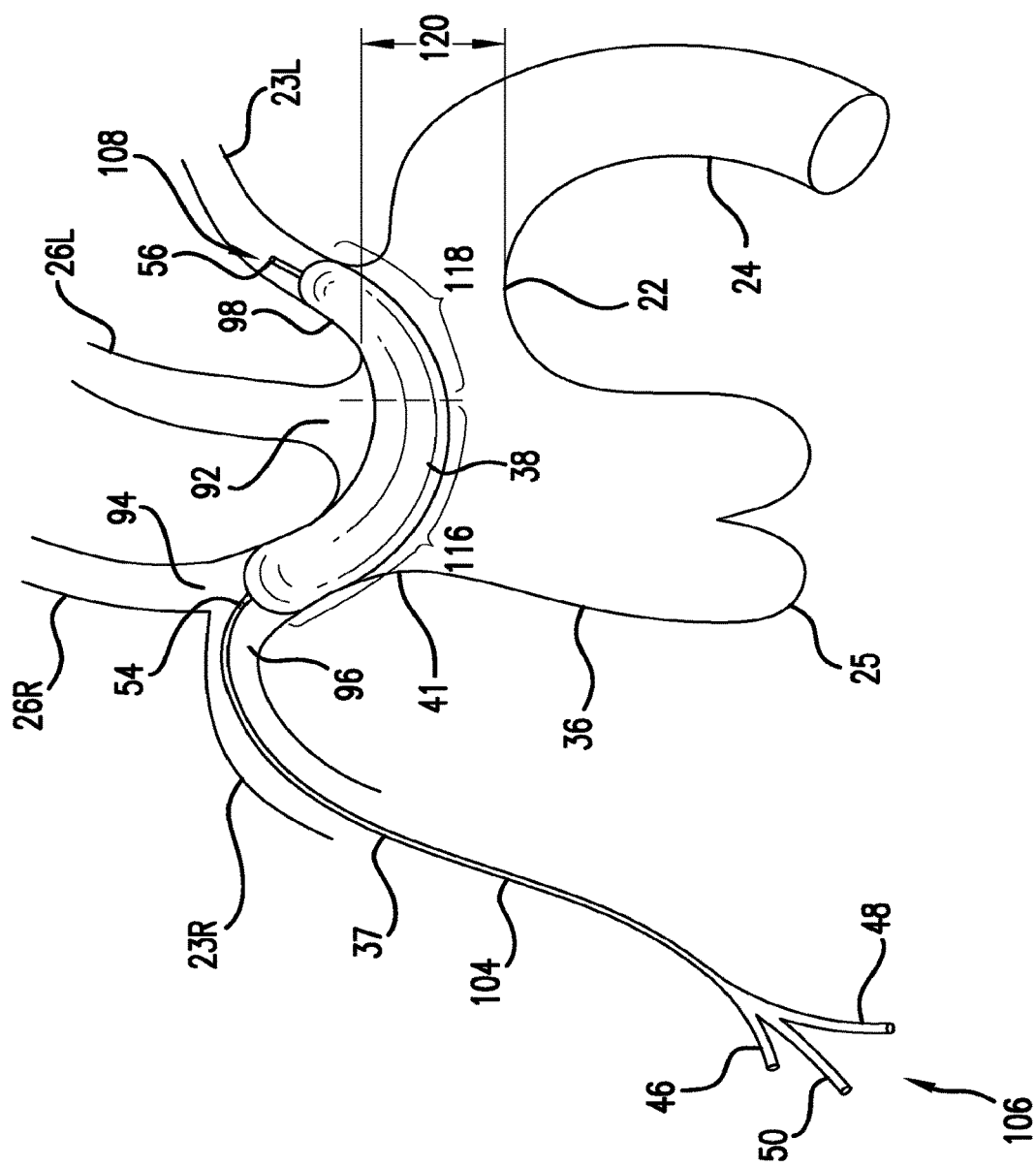
FIG. 14 is a front view of the patient with the occluding catheter of FIG. 13 in an inflated state.

Another exemplary embodiment of the occluding catheter 37 is shown in FIGS. 13 and 14. This embodiment achieves a temporary interruption of cerebral arterial inflow without placing the occluding catheter 37 into carotid arteries 26L and 26R by creating a single occluding balloon 38 extending the distance between the bifurcation of the innominate artery 41 and the orifice 98 of a left subclavian artery 23L. The single occluding balloon 38 may be provided so that no other occluding balloons, and in some instances no other balloons at all, are present on the occluding catheter 37.

When inflated, the occluding balloon 38 will effectively occlude the orifice of the right subclavian artery 96, the orifice of the right carotid artery 94, the orifice of the left carotid artery 92, and the orifice of the left subclavian artery 98 which are all branches of the aortic arch 22. This inflation will block flow into the brain by blocking flow through the right and left carotid arteries 26R and 26L and through both the right subclavian and left subclavian arteries 23R and 23L and, therefore, both right and left vertebral arteries. The occluding catheter 37 in this arrangement achieves complete avoidance of any manipulations on the carotid arteries 26R and 26L, thus eliminating the risk of induced injury or emboli 28, leading to stroke, problems that are known to occur in the prior art devices. As shown, the occluding balloon 38 is not located within the right or left carotid arteries 26R, 26L when inflated. The occluding balloon 38 may also not be located within the right subclavian artery 23R when inflated in some embodiments.

The occluding catheter 37 may be inserted via the peripheral artery of the right or left arm. FIGS. 13 and 14 show introduction through the right arm for vascular access. A guide wire 100 may first be passed via the brachial artery and advanced first into the innominate artery 41, then the aortic arch 22, and finally into the left subclavian artery 23L. The occluding catheter 37 will be next advanced over the guide wire 100 and consequently first into the innominate artery 41, then the aortic arch 22 and finally into the left subclavian artery 23L. The occluding balloon 38 extends from the level of the innominate artery 41 to the level of the left subclavian artery 23L.

Figure 15:
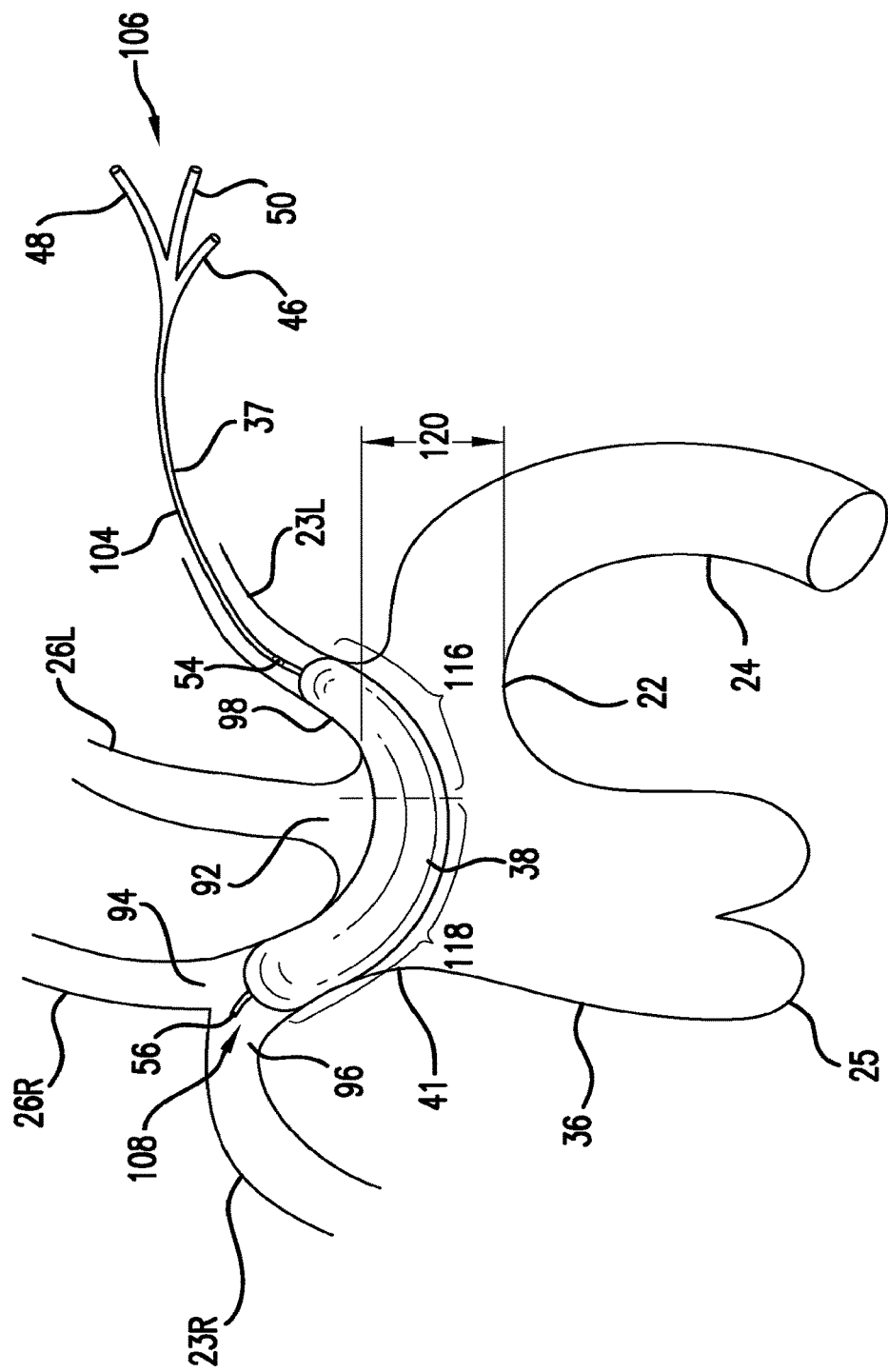
FIG. 15 is a front view of the patient with the occluding catheter of FIG. 13 in an inflated state but introduced instead through a left subclavian artery in accordance with a still further exemplary embodiment.

The left arm is used for insertion as shown in FIG. 15. The occluding catheter 37 is first advanced into the left subclavian artery 23L, then the aortic arch 22, and then into the innominate artery 41 and right subclavian 23R artery. The occluding balloon 38 extends through the whole distance between the left and right subclavian arteries 23L, 23R. Inflation of the occluding balloon 38 occludes the orifices 96, 94, 92, and 98 to completely prevent the emboli 28 from entering cerebral circulation via all potential ways of arterial inflow. Pressure in the right subclavian artery 23R may be measured using the distal tip opening 56, and opening of the shaft 54 can be used to measure blood pressure in the left subclavian artery 23L.

Although the occluding balloon 38 is a single occluding balloon introduced through the left arm of the patient in FIG. 15, should the occluding catheter 37 include proximal and distal occluding balloons 38, 42 and be desired for insertion through the left arm the relative occluding balloon 38, 42 sizes may be varied. For example, the distal occluding balloon 42 may be larger in diameter 112 than the diameter 110 of the proximal occluding balloon 38. The distal occluding balloon 42 when inflated may block flow through the innominate artery 41, and the proximal occluding balloon 38 would block flow through the left carotid artery 26L. The segment 44 would be between the balloons 38, 42 and would be located in the aortic arch 22. The proximal portion of the occluding catheter 37 may be located within the left subclavian artery 23L. Placement may be effected by first inflating the distal occluding balloon 42 to allow arterial blood flow to naturally pull it into the innominate artery 41. The distal occluding balloon 42 may be deflated to allow for determination of the positioning of the occluding catheter 37. The proximal occluding balloon 38 may be inflated to determine its positioning as it may block flow through both the left carotid artery 26L and the left subclavian artery 23L.

Although described as blocking flow through both of the carotid arteries 26R and 26L, it is to be understood that only one of the carotid arteries 26R or 26L may be blocked in certain arrangements and uses of the occluding catheter 37.

The size and shape of the occluding balloon 28 can vary depending on the patient's anatomy and the size of the arteries discussed herein. For this purpose it may be the case that low pressure, highly compliant occluding balloons 38 of conical and ovoid shape are used with larger central segments corresponding to the patient's innominate artery 41, and aortic arch 22, and the narrower peripheral segments corresponding to the level of right and left subclavian arteries 23R and 23L. The large segment of the occluding balloon 38 should be large enough to occlude the innominate artery 41 and the orifice 92 of the left carotid artery 23L, but not too large to compromise the lumen of the aortic arch 22. It may be made sufficiently compliant to assure slight herniation into the orifices 96, 94, 92 and 98 during inflation. Thus in some arrangements, the occluding balloon 38 may extend into any one of or all of the arteries 23R, 26R, 26L and 23L.

The diameter 120 of the aortic arch 22 is larger than the diameter 110 of the occluding balloon 38 when the occluding balloon 38 is inside of aortic arch 22 and is inflated. This arrangement will block blood flaw through the carotid arteries 26R, 26L but will allow for divergence of blood flow carrying the emboli 28 into the distal aorta 24 and away from the cerebral circulation. The maximal diameter 110 of this segment of the occluding balloon 38 within the aortic arch 22 may not exceed 60-70% of the diameter 120 of the aortic arch 22. In other arrangements, the diameter 110 within the aortic arch 22 may be up to 25%, up to 35%, 50%, or up to 60% of the diameter 120.

Although described as preventing emboli 28 from flowing through the carotid arteries 26R, 26L, the occluding catheter 37 may also be used to prevent emboli 28 from flowing through the right subclavian artery 23R and/or the left subclavian artery 23L. This prevention may be in addition to or alternatively to prevention of flow through the carotid arteries 26R and/or 26L.

The occluding catheter 37 may be wireless in that it can be placed within the patient without the use of a guide wire 100. When provided with a pair of occluding balloons 38 and 42, the distal occluding balloon 42 may be referred to as a "floating" balloon to allow for wireless catherization of the aortic arch 22 branches. The distal occluding balloon 42 may be fully or partially inflated and through the size of the fully or partially distal occluding balloon 42 will be propelled into one of the branches 23L, 26L, 41 of the aortic arch 22 while the occluding catheter 37 is gently advanced or pulled back (manipulated) until it reaches the target artery. The desired location of the distal occluding balloon 42 may be the left carotid artery 26L or left subclavian artery 23L if the occluding catheter 37 is inserted via the right arm of the patient. The desired location of the distal occluding balloon 42 may be the right subclavian artery 23R, the Innominate artery 41, or the right carotid artery 26R if the occluding balloon 42 is inserted via the left arm of the patient. In other arrangements, when a single occluding balloon 38 is used instead of a distal occluding balloon 42 and a proximal occluding balloon 38, the single occluding balloon 38 may also be drawn into one of the aforementioned branches of the aortic arch 22 via natural blood flow pulling and be a wireless placement.

The occluding balloon 38, or the proximal occluding balloon 38 and distal occluding balloon 42 when two are present, and the shaft 104 are arranged so that when inflated all of the blood into the artery in question (23L, 26L, 26R, 23R and/or 41) is blocked. In this regard, no blood flows past the inflated balloon 38 or 38, 42 or the shaft 104. Blood does not flow through any channel or any portion of the shaft 104 into any of the arteries 23L, 26L, 26R, 23R and/or 41. The arteries 23L, 26L, 26R, 23R and/or 41 may be completely prevented from having blood flowing through them as per the arrangement of all portions of the occluding catheter 37. The segment 44 may be arranged so that access to an inner channel of the shaft 104 is not possible. In this regard, the segment 44 may be solid and capable of blocking blood flow such that no blood enters segment 44 when the occluding balloons 38 and 42 are inflated and are located in the patient. The shaft 104 is arranged so that blood does not flow from the aortic arch 22 into the shaft when the occluding catheter 37 is oriented in the patient and used to reduce emboli 28 through the carotid arteries 26R, 26L.

In other arrangements, the occluding balloon 38, or proximal occluding balloon 38 and distal occluding balloon 42 when two are present, and the shaft 104 are arranged so that some blood does flow into arteries 23L, 26L, 26R, 23R and/or 41. The balloon 38 or 38, 42 can be partially inflated but not inflated all the way to seal the arterial wall. The balloon 38 or 38, 42 can be made so that even if fully inflated it is small enough not to completely block blood flow to seal the arterial wall. Some amount of blood can in fact flow past the inflated balloon 38 or 38, 42 and into the various arteries 23L, 26L, 26R, 23R and/or 41. The blood that flows past is unfiltered blood. Although emboli 28 may still flow into cerebral circulation and cause stroke, even partial reduction of flow will cause a partial reduction in the chance of stroke or the severity of stroke. The occluding catheter 37 may block from 30%-50%, from 50%-70%, from 70%-90% or up to 100% of the blood flow into the various arteries 23L, 26L, 26R, 23R and/or 41 in accordance with certain exemplary embodiments. Blood that does flow into the various arteries 23L, 26L, 26R, 23R and/or 41 comes directly from the aortic arch 22 and is unfiltered. As used herein, the term "occlude" is broad enough to include complete blockage of blood flow and to include partial blockage of blood flow while still allowing some unfiltered blood to flow through. Also, as used herein when referring to a "block" of blood flow, it is to be understood that this term is broad enough to cover complete blocking of blood flow and partial blocking of blood flow such that some amount of unfiltered blood flows through.

In use, the occluding catheter 37 may be used so that partial inflation or total inflation of the occluding balloons 38 or 38, 42 is made during a medical procedure to control the blood flow through by reducing the risk of stroke while still allowing blood to enter the cerebral circulation. When fully inflated to completely block blood flow, the occluding balloons 38 or 38, 42 are solid components and not filters and do not filter emboli 28 but rather prevent everything including blood and emboli 28 from moving therethrough. The occluding balloons 38 or 38, 42 and tube sections of the occluding catheter 37 may completely block blood and emboli 28 from moving through the particular blood vessel such that no blood or emboli 28 flows through the tube sections of the occluding catheter 37 past the occluding balloons 38 or 38, 42. The occluding balloons 38 or 38, 42 and the tubular sections of the occluding catheter 37 located at the blocked area of blood/emboli 28 flow when positioned are not porous members and do not filter any blood. However, when the occluding balloons 38 or 38, 42 are deflated, partially deflated, or fully inflated but less than the diameter of the vessel they are in allow blood and emboli 28 to flow around them through the particular blood vessel and they are not filtered in any manner, although the flow rate may be decreased due to the presence of the occluding balloons 38 or 38, 42 and tubular sections of the occluding catheter 37.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. An occluding catheter for preventing stroke by occluding blood flow through a right carotid artery and a left carotid artery of a patient, comprising:
   a shaft that has a proximal end and a distal end;
   a proximal occluding balloon carried by the shaft, wherein the proximal occluding balloon is inflated to occlude blood flow through one of the right carotid artery and the left carotid artery;
   a distal occluding balloon carried by the shaft, wherein the distal occluding balloon is inflated to occlude blood flow through one of the right carotid artery and the left carotid artery that is not occluded by the proximal occluding balloon;
   wherein the shaft has a segment that is located between the proximal occluding balloon and the distal occluding balloon; and
   an alarm system that activates a pressure supply to the proximal occluding balloon and the distal occluding balloon to cause inflation when microemboli are detected, and wherein the alarm system deflates the proximal occluding balloon and the distal occluding balloon when the proximal and distal occluding balloons remain inflated for a cut-off period of time, and wherein the alarm system has a manual override to prevent inflation and deflation by the alarm system.

2. The occluding catheter as set forth in claim 1, wherein the proximal occluding balloon is located within an innominate artery of the patient and completely occludes blood flow through the right carotid artery and through a right subclavian artery of the patient, wherein the distal occluding balloon is located within the left carotid artery and completely occludes blood flow through the left carotid artery.

3. The occluding catheter as set forth in claim 2, wherein the proximal occluding balloon has a diameter that is greater than a diameter of the distal occluding balloon.

4. The occluding catheter as set forth in claim 1, wherein the shaft has a proximal occluding balloon channel that extends from the proximal occluding balloon to a proximal occluding balloon inflation port located at the proximal end of the shaft, wherein the shaft has a distal occluding balloon channel that extends from the distal occluding balloon to a distal occluding balloon inflation port located at the proximal end of the shaft, wherein the distal occluding balloon channel and the proximal occluding balloon channel are not in fluid communication with one another.

5. The occluding catheter as set forth in claim 1, wherein the shaft has an end pressure measurement channel that extends from a distal tip opening of the shaft located at the distal end of the shaft to an end pressure measurement port located at the proximal end of the shaft.

6. The occluding catheter as set forth in claim 5, wherein the distal end is located within the left carotid artery, wherein the distal tip opening is located distally from the distal occluding balloon.

7. The occluding catheter as set forth in claim 1, wherein the shaft has an intermediate pressure measurement channel that extends from an opening of the shaft located proximal to both the proximal occluding balloon and the distal occluding balloon to an intermediate pressure measurement port located at the proximal end of the shaft.

8. The occluding catheter as set forth in claim 1, wherein a guide wire is not disposed through any portion of the shaft.

9. An occluding catheter for preventing stroke by occluding blood flow through a right carotid artery and a left carotid artery of a patient, comprising:
   a shaft that has a proximal end and a distal end;
   an occluding balloon carried by the shaft, wherein the occluding balloon is inflated to occlude blood flow through both the right carotid artery and the left carotid artery; and
   an alarm system that activates a pressure supply to the occluding balloon to cause inflation when microemboli are detected, and wherein the alarm system deflates the occluding balloon when the occluding balloon remain inflated for a cut-off period of time, and wherein the alarm system has a manual override to prevent inflation and deflation by the alarm system.

10. The occluding catheter as set forth in claim 9, wherein the occluding balloon has a proximal portion and a distal portion, wherein the proximal portion is larger than the distal portion, wherein the proximal portion is located within an innominate artery of the patient and completely occludes blood flow through the right carotid artery and through a right subclavian artery of the patient, wherein the distal portion is located within the left carotid artery and completely occludes blood flow through the left carotid artery.

11. The occluding catheter as set forth in claim 9, wherein the shaft has an occluding balloon channel that extends from the occluding balloon to an occluding balloon inflation port located at the proximal end of the shaft, wherein the shaft has an end pressure measurement channel that extends from a distal tip opening of the shaft located at the distal end of the shaft to an end pressure measurement port located at the proximal end of the shaft, and wherein the shaft has an intermediate pressure measurement channel that extends from an opening of the shaft located proximal to both the occluding balloon and the distal tip opening to an intermediate pressure measurement port located at the proximal end of the shaft.

12. The occluding catheter as set forth in claim 11, further comprising a guide wire that extends through the end pressure measurement port and through the end pressure measurement channel and extends out of the distal tip opening.

13. The occluding catheter as set forth in claim 9, wherein the occluding balloon has a segment that is uninflated that separates the occluding balloon into a proximal portion and a distal portion.

14. The occluding catheter as set forth in claim 9, wherein the occluding balloon is located within an aortic arch, a left subclavian artery, and an innominate artery of the patient, and wherein the occluding balloon is not located within the left carotid artery of the patient.

15. The occluding catheter as set forth in claim 14, wherein the occluding balloon is not located within the right carotid artery of the patient.

16. The occluding catheter as set forth in claim 14, wherein the occluding balloon has an amount of flexibility and mobility to be advanced with a forward blood flow into branches of an aortic arch, including a left carotid artery, a right carotid artery, a left subclavian artery, a right subclavian artery, and an innominate artery of the patient to allow for wireless catheterization and occlusion of said arteries.

17. The occluding catheter as set forth in claim 9, wherein the occlusion that the occluding balloon performs is partial occlusion such that unfiltered blood flows past the inflated occluding balloon and through both the right carotid artery and the left carotid artery.

\* \* \* \* \*